United States Patent [19]

Sato

[11] Patent Number: 5,394,245
[45] Date of Patent: Feb. 28, 1995

[54] PROCESS AND APPARATUS FOR MEASURING PRETILT ANGLE OF LIQUID CRYSTALS

[75] Inventor: Shigehiro Sato, Osaka, Japan

[73] Assignee: Matsushita Electric Industrial Co., Ltd., Osaka, Japan

[21] Appl. No.: 115,702

[22] Filed: Sep. 3, 1993

[30] Foreign Application Priority Data

Sep. 4, 1992 [JP] Japan .................. 4-236794

[51] Int. Cl.[6] ............................ G01N 21/21
[52] U.S. Cl. ..................... 356/369; 356/364
[58] Field of Search ............ 356/364, 365, 366, 367, 356/368, 369, 370

[56] References Cited

U.S. PATENT DOCUMENTS 5,172,187 12/1992 Brosig ............................. 356/364
5,245,403 9/1993 Kato et al. ...................... 356/237

FOREIGN PATENT DOCUMENTS 1-162134 6/1989 Japan .

OTHER PUBLICATIONS

Scheffer et al., "Accurate Determination of Liquid—Crystal Tilt Bias Angles", Journal of Applied Physics, vol. 48, No. 5, pp. 1783–1792 (May 1977).

Primary Examiner—Richard A. Rosenberger
Attorney, Agent, or Firm—Wenderoth, Lind & Ponack

[57] ABSTRACT

The present invention relates to a method and apparatus for measuring a pretilt angle. The pretilt angle is measured as follows: an alignment layer and a liquid-crystal layer each of which has a refractive index smaller than that of a substrate are laminated on the substrate, a polarized light is emitted into the substrate and made to be reflected on an interface between the substrate and the alignment layer to measure a reflectance, and a ratio of logarithm of reflectances of lights crossing each other is calculated to give a pretilt angle. The apparatus for measuring a pretilt angle comprises a system keeping at least a substrate, a photo system composed of a light source which emits a linear polarized light into the substrate, a detecting system for measuring reflectance of light reflected inside the substrate, and a data-processing system which calculates a pretilt angle from a ratio of logarithm of reflectances of polarized lights crossing each other.

11 Claims, 2 Drawing Sheets

PROCESS AND APPARATUS FOR MEASURING PRETILT ANGLE OF LIQUID CRYSTALS

BACKGROUND OF THE INVENTION

1. Field of the Invention

The present invention relates to a liquid crystal, an alignment layer and an alignment process, which are applied to a liquid-crystal display device. More particularly, the present invention relates to a process and an apparatus for measuring pretilt angle of liquid crystals, which are applied to a TFT liquid-crystal display device and a STN liquid-crystal display device.

2. Description of the Prior Art

Two kinds of methods for measuring a pretilt angle, which means an angle of liquid-crystal director to a substrate face, are well used. One of them is known as a magneto-capacitive null method and the other is known as a crystal rotation method. These measuring methods are described in detail in Journal of Physics, Vol. 48, No. 5, p. 1783–1792 (1977).

The magneto-capacitive null method is described as follows: A liquid-crystal cell is prepared. Then a capacity is measured while the liquid-crystal cell is rotated. When the same capacity as the one measured in no magnetic field is given, the rotation angle is referred to as a pretilt angle.

The crystal rotation method is described as follows: A liquid-crystal cell is prepared. Then polarized light is emitted into the liquid-crystal cell at angle of 45 degrees to a rubbing direction. The cell is rotated and light-transmittance is measured. A fringe of light-transmittance to a rotation angle becomes symmetric at a certain degree. A pretilt angle is calculated from the wavelength of the light, the symmetric angle and refractive index of liquid crystals.

The above methods for measuring a pretilt angle have the following defects. In the magneto-capacitive null method, it is hard for liquid crystals to align in a magnetic field unless a thickness of liquid-crystal cell is 10 μm or more, as a result of which it becomes difficult to measure a pretilt angle. In the crystal rotation method, it is difficult to determine a symmetric angle accurately unless a thickness of liquid-crystal cell is 10 μm or more, as a result of which a pretilt angle can not be measured.

SUMMARY OF THE INVENTION

The object of the present invention is to provide a process and an apparatus for measuring a pretilt angle of liquid crystals without being influenced by thickness of liquid-crystals.

The present invention relates to a method for measuring a pretilt angle in which an alignment layer and a liquid-crystal layer each of which has a refractive index smaller than that of a substrate are laminated on the substrate, a polarized light is emitted into the substrate and made to be reflected on an interface between the substrate and the alignment layer to measure a reflectance and a ratio of logarithm of reflectances of lights crossing each other is calculated.

The present invention also relates to an apparatus for measuring a pretilt angle which comprises a system keeping at least a substrate, a photo system composed of a light source which emits a linear polarized light into the substrate,
a detecting system for measuring reflectance of light reflected inside the substrate, and
a data-processing system which calculates a pretilt angle from a ratio of logarithm of reflectances of polarized lights crossing each other.

DETAILED DESCRIPTION OF THE INVENTION

Figure 1:
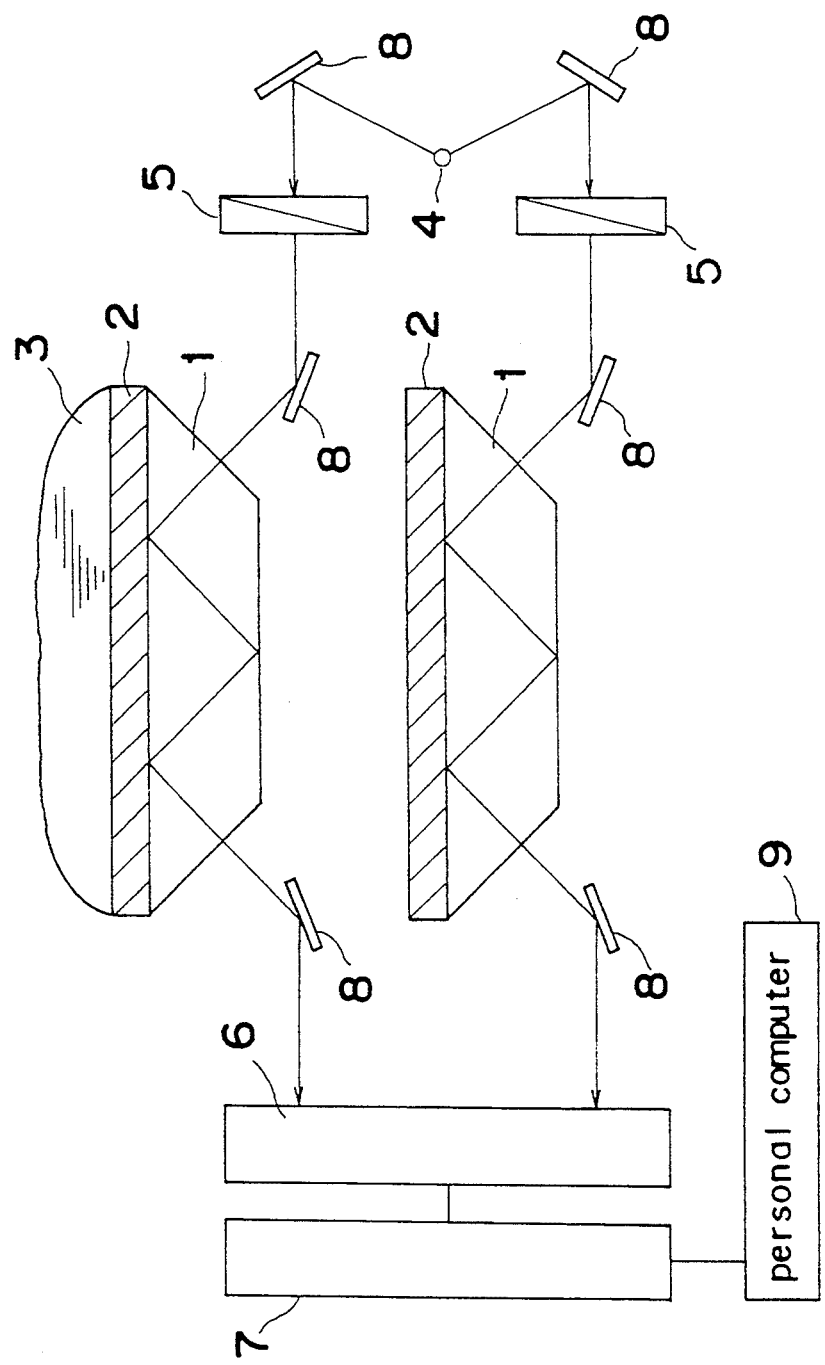
FIG. 1 is a block diagram of one example of an apparatus for measuring a pretilt angle according to the present invention.

The above object can be achieved by measuring a pretilt angle in accordance with the following process. An alignment layer and a liquid-crystal layer each of which has a refractive index smaller than that of a substrate are laminated on the substrate. Then polarized lights crossing each other are emitted respectively into the substrate and made to be total-reflected on an interface between the substrate and the alignment layer to measure reflectances. A ratio of logarithm of the two reflectances are calculated. A pretilt angle is given on the basis of the ratio.

An apparatus for measuring a pretilt angle comprises at least:

a keeping system for a substrate,
a photo system composed of a light source which emits a linear polarized light into the substrate,
a detecting system for measuring reflectance of light reflected inside the substrate, and
a data-processing system which calculates a pretilt angle from a ratio of logarithm of reflectances of polarized lights crossing each other.

The constitution above makes it possible to measure a pretilt angle. The polarized light emitted into the substrate not only reflects on an interface between the substrate and the alignment layer but also penetrates partially the alignment layer and the liquid crystal layer. A substrate and an incident angle are selected suitably depending on a thickness of liquid-crystal layer because a penetration depth depends on a wavelength of measuring light, a refractive index of liquid crystal and substrate and an incident angle.

A logarithm of reflectance of total-reflected light corresponds to an absorbance of light absorbed into an alignment layer and a liquid crystal layer. A ratio of a logarithm of a reflectance in the case where an electric field vector of light is parallel to a reflecting face, to a logarithm of a reflectance in the case where the electric field vector of light is perpendicular to the reflecting face (this ratio corresponds to a dichroic ratio of absorbances) is related with a pretilt angle ($\gamma$), an angle ($\beta$) formed between a director of liquid crystal and a transition moment for light absorption, and an order parameter (S). The angle ($\beta$) and the order parameter (S) may be measured by other methods. Therefore the pretilt angle can be determined univocally from a ratio of logarithms of reflectances.

Once a calibration curve is drawn up in the relation between a dichroic ratio (Dsp) and a pretilt angle measured by another method, it becomes easier to obtain a pretilt angle because it is not necessary to measure S and $\beta$ which are uncertain factors. Even though a thickness of alignment layer, a rubbing strength or a kind of alignment layer is changed, this calibration curve does not vary so far as a kind of liquid crystal, an incident angle and a wavelength of measuring light are fixed.

An absorbance given from a reflectance of total-reflected light corresponds to the value made by (an absorbance given when an alignment layer is not formed) X (a correction factor related to an alignment layer thickness) when the alignment layer does not absorb a measuring light.

As above explained, it becomes possible according to the present invention to measure a pretilt angle of liquid crystals in a liquid crystal cell having a liquid-crystal layer thickness of 10 μm or less when a measuring wavelength, a substrate material and an incident angle are adequately selected. Such a pretilt angle can not be measured in a conventional method.

A pretilt angle of liquid crystals can be measured without preparation of a liquid crystal cell. It becomes also possible to measure a pretilt angle of super twisted nematic liquid crystals having a twisting angle of about 270 degrees. Such a pretilt angle also can not be measured in a conventional method. According to the present invention, it becomes easier to select a liquid crystal and rubbing conditions. Further, distribution of pretilt angle in a liquid crystal cell can be measured by changing a position where a measuring light is total-reflected. By taking the distribution into consideration, most suitable conditions for preparing a cell may be selected in such a way that nonuniformity of pretilt angle is made small. As a result, a pretilt angle of liquid crystals can be controlled when a liquid crystal panel is produced in an industrial process, as a result of which the quality of a liquid crystal display device can be made high and yield can be improved.

FIG. 1 is a block diagram of one example of an apparatus for measuring a pretilt angle according to the present invention. The present invention is explained by referring to FIG. 1.

A process for measuring a pretilt angle comprises the following three steps:
  a sample-preparing step in which an alignment layer (2) and a liquid-crystal layer (3) each of which has a refractive index smaller than that of a substrate (1) are laminated on the substrate (1),
  a measuring step in which a polarized light is emitted into the substrate (1) and made to be total-reflected on an interface between the substrate (1) and the alignment layer (2) to measure a reflectance, and
  a data-processing step in which a ratio of logarithm of reflectances of lights crossing each other is calculated.

The sample prepared in the sample-preparing step has the alignment layer (2) formed on the substrate (1) which makes a measuring light pass through and total-reflect on the interface. The liquid crystal layer (3) is laminated on the layer (2).

A material having a refractive index higher than that of the alignment layer (2) and that of the liquid crystal layer (3) may be applied as the substrate (1). The alignment layer (2) and the liquid crystal layer (3) usually have respectively a refractive index of about 1.5. Silicon (Si), Germanium (Ge) and Zinc Selenide (ZnSe) may be applied as the substrate (1) when a measuring light is infrared rays. A refractive index of Si is 3.5. A refractive index of Ge is 4. A refractive index of ZnSe is 2.7. Sapphire may be used in the case of ultraviolet rays. A refractive index of sapphire is 1.8. It is necessary that the shape of the substrate (1) is processed such that an incident light can total-reflect inside the substrate. When a sectional view of the substrate (1) a is parallelogram or trapezoid, it is advantageous to keep an incident angle constant.

The alignment layer (2) is formed on the substrate (1). A layer thickness of the alignment layer (2) is adjusted to be much thinner than a penetration depth of a measuring light, thereby a S/N ratio may be advantageously improved. A penetration depth (dp) of a measuring light into the alignment layer (2) or the liquid crystal layer (3) may be calculated according to the following formula:

$$dp = \frac{\lambda}{2\pi n_1} \left[ \sin^2\theta - \left(\frac{n_2}{n_1}\right)^2 \right]^{-\frac{1}{2}}$$

in which $n_1$ means a refractive index of the substrate (1), $n_2$ means a refractive index of the alignment layer (2) or the liquid crystal layer (3), $\lambda$ means a wavelength of measuring light, $\theta$ means an incident angle of a measuring light to a total-reflecting face of the substrate (1). For example, the penetration depth of 0.66 μm is given when a measuring light is an infrared ray having a wavelength ($\lambda$) of 10 μm, a refractive index of the substrate (1) is 4.0, a refractive index of the alignment layer (2) and the crystal liquid layer (3) is 1.5 respectively, and an incident angle ($\theta$) is 45 degrees. Therefore the alignment layer (2) is formed such that the layer has a thickness much thinner than 0.66 μm. In general, a layer thickness of the alignment layer (2) in a liquid crystal display device is about 0.05 μm, which is favorable because the thickness is much thinner than the penetration depth.

A material for forming the alignment layer (2) is selected from the ones having a refractive index smaller than the substrate (1). Such a material is exemplified by polyimide, polyvinyl alcohol and polystyrene. Polyimide is preferable.

The alignment layer (2) may be formed, for example, by being subjected to an aligning treatment after formation of an alignment layer on the substrate (1) by a conventional coating method, or by aligning molecules on the substrate (1) by a LB method or a deposition method. The aligning treatment is exemplified preferably by a known rubbing method because it is similar to a practical production method. Most suitable aligning direction is parallel or perpendicular to an advancing direction of a measuring light.

Then the crystal liquid layer (3) is formed on the alignment layer (2). A thickness of the liquid crystal layer (3) is not particularly limited so far as it is much thicker than a penetration depth of a measuring light. The thickness of the liquid crystal layer may be somewhat nonuniform. But the extremely nonuniform thickness causes nonuniform pretilt angles because of elastic properties of liquid crystals.

The measuring step is explained below.

A measuring light is divided into a sample light and a reference light. The divided lights are led respectively into a substrate (1) through a polarizer (5) as a linear polarized light. The sample light and the reference light total-reflect respectively inside the substrate (1) and the lights are separated into its spectral components by a monochrometer and reach a detector.

The light source is not limited. It is, however, necessary that a liquid crystal layer (3) has anisotropy for absorbance and that a light which is not absorbed in an alignment layer (2) is selected. Infrared rays and ultraviolet rays may be used. The light penetrates into the alignment layer (2) and the liquid crystal layer (3) at the time of total reflection. As a wavelength of light becomes shorter, a pretilt angle of liquid crystals near the surface of the alignment layer (2) can be measured. A wavelength of light may be selected according to objects. Infrared rays are most preferable as the light source (4) because a pretilt angle of each liquid crystal component can be measured.

When an infrared ray is used as the light source (4), it is necessary to use such a wavelength that the liquid crystal layer (3) displays anisotropy of absorbance. Absorbance peaks caused by stretching vibration of a carbonyl group or a cyano group, or out-of-plane deformation of an aromatic ring may be used. It is most advantageous to use a wavelength corresponding to absorbance caused by out-of-plane deformation of an aromatic ring of a liquid crystal molecule because a molecular long axis often crosses a transition moment for absorbance. Any kind of polarizer (5) may be used so far as a measuring light can be changed to a linear polarized light. However it should be noticed that a polarizer which has so low polarizing performance can not give an accurate dichroic ratio.

In the measuring process, the polarizer is set such that a reflecting surface of total-reflection is parallel to an electric field vector of light. Then a mirror (8) is set such that a measuring light is led to the polarizer (5), the substrate (1), the monochromer (6) and the detector (7) in this order, so that a reflectance (Rp) is measured. Then the polarizer is set such that a reflecting surface of total-reflection crosses an electric field vector of light to measure a reflectance (Rs). A reflected-light strength is divided by an incident-light strength to give a reflectance. With respect to the incident-light strength, it is convenient to use a reflected-light strength measured in the case where the liquid crystal layer (3) is not formed on the alignment layer (2) formed on the substrate because reflectance is not influenced by the substrate and absorbance into an alignment layer. The monochrometer (6) and the detector (7) may be known ones, so far as a measuring light can be separated into its spectral components and that a light strength of desired wavelength can be measured. When infrared rays are used, a diffraction grating may be used as the monochromer (6) and a thermocouple may be used as the detector (7). A known spectrophotometer may be used because the monochrometer (6), the detector (7) and the light source (4) are all installed.

In the data processing process, a ratio of logarithms of reflectances of polarized lights crossing each other (a dichroic ratio of absorbance)(Dsp) is calculated according to the following formula:

$$Dsp = -\log(Rs)/-\log(Rp)$$

This Dsp can be easily calculated by the application of a personal computer (9) available in the market to the data processing system. When a spectrophotometer for infrared rays or ultraviolet rays available in the market is used, a logarithm of reflectance is given as an absorbance. In this case, a ratio of absorbances of polarized lights crossing each other is calculated in the data processing system. Dsp corresponds to a pretilt angle univocally. For example, when an aligning direction is perpendicular to an advancing direction of a measuring light, the relationship between Dsp and a pretilt angle ($\gamma$) can be given as the following formula:

$$\frac{1}{Dsp} = \frac{q\{3S\sin^2\beta + 2(1-S)\} + r\{3S\sin^2\beta + 2(1-S) + 3S(2-3\sin^2\beta)\cos^2\gamma\}}{p\{3S\sin^2\beta + 2(1-S) + 3S(2-3\sin^2\beta)\sin^2\gamma\}}$$

In the above formula, the symbol $\gamma$ represents a pretilt angle which means an angle of liquid-crystal director to a substrate normal, the symbol S represents an order parameter of the liquid crystal layer (3), the symbol $\beta$ represents an angle formed between a transition moment for desired absorbance and a director of liquid crystal molecule. The symbols p, q, r are parameters depending on refractive indexes of the liquid crystal layer (3) and the substrate (1), and an incident angle of a measuring light. The S and $\beta$ can be given by measuring permeation infrared absorption.

It is more preferable to prepare in advance a calibration curve for pretilt angles measured by some other method in order to determine a pretilt angle. A pretilt angle is given quickly on the basis of the calibration curve when Dsp is given.

In the apparatus for measuring a pretilt angle shown in FIG. 1, a light emitted from a light source is divided into a reference light and a measuring light to measure a reflectance. However the present invention is not limited to such a type. For example, a spectrosystem of Fourier transform type may be used.

Preferably a system which can keep an alignment layer on the substrate (1) horizontal is installed in an apparatus for measuring a pretilt angle. Thereby it becomes possible to drop liquid crystals from the outside of the measuring apparatus.

Concrete examples are explained hereinafter.

EXAMPLES 1-3

Samples were prepared as follows. A material of substrate was germanium. The size of the substrate was 25 mm × 10 mm × 3 mm. The sectional view of the substrate was parallelogram. An angle of the parallelogram was 45 degrees so that an incident light might be perpendicular to an incident face. The surface of substrate was coated with polyimide varnish as a material of alignment layer available in the market as SE 150 (made by Nissan Chemical Industries Ltd)(in Example 1), SE4110 (made by Nissan Chemical Industries Ltd) (Example 2) and PSI2201 (made by Chisso Petrochem Co.) (Example 3) as shown in Table 3. The coated polyimide varnish was heat-treated at 250° C. for 2 hours. A thickness of the alignment layer was adjusted to be 50 nm. Then the substrate was subjected to a rubbing treatment. In this process, the surface of alignment layer on the substrate was buffed with rayon velvet. Thus an alignment layer made of polyimide varnish was formed.

A glass substrate the size of which was 25 mm × 15 mm × 1.1 mm was laminated on the alignment layer with a spacer interposed between the layer and the glass substrate at a space of 4 µm. In this case the glass substrate and the alignment layer were arranged facing each other and the glass substrate was bonded to the germanium substrate having the alignment layer thereon.

Then the space between the germanium substrate and the alignment layer was filled with 4-(trans-4'-n-pentylcyclohexyl)-benzonitrile as a liquid crystal material. Thus a sample for measuring a pretilt angle was prepared. The sample was kept at 80° C. for 1 hour to stabilize an pretilt angle.

A reflectance inside the germanium substrate of the sample was measured by means of an infrared spectrometer as follows. A mirror was set so that a measuring light might pass through a polarizer to reach the sample. The sample was adjusted so that the incident light might reach a total-reflection face inside the germanium substrate at an incident angle of 45 degrees. A polarizer was set so that the total-reflection face might be parallel to an electric field vector. Thus a reflectance (Rp) was measured. Then the polarizer was set so that the total-reflection face might cross the electric field vector. Thus a reflectance (Rs) was measured. In this process attention was paid to absorbance of 833 cm$^{-1}$ caused by out-of-plane deformation of an aromatic ring in the liquid crystals. Further a dichroic ratio Dsp was calculated according to the following formula:

$$Dsp = -log(Rs)/-log(Rp)$$

The result of the calculation was shown in Table 3.

EXAMPLES 4–6

Samples were prepared as follows. A substrate made of the same material as that in Examples 1–3 but having a sectional view of trapezoid was used. Polyimide varnish as a material of alignment layer available in the market as SE 150 (made by Nissan Chemical Industries Ltd)(in Example 4), SE4110 (made by Nissan Chemical Industries Ltd)(Example 5) and PSI2201 (made by Chisso Petrochem Co.)(Example 6) as shown in Table 3 was applied on the substrate in a manner similar to Examples 1–3, followed by a rubbing treatment to form an alignment layer.

Then 4-(trans-4'-n-pentylcyclohexyl)-benzonitrile was dropped onto the alignment layer as a liquid crystal. Thus a sample for measuring a pretilt angle was prepared. The sample was kept at 80° C. for 1 hour to stabilize an pretilt angle.

An incident light was total-reflected inside the substrate of the sample to measure a reflectance by means of an infrared spectrometer. At that time, the sample was set to be horizontal.

The measurement of a pretilt angle was carried out as follows. First, a polarizer was set so that the total-reflection face might be parallel to an electric field vector. Thus a reflectance (Rp) was measured. Then the polarizer was set so that the total-reflection face might cross the electric field vector. Thus a reflectance (Rs) was measured. In this process attention was paid to absorbance of 833 cm$^{-3}$ caused by out-of-plane deformation of an aromatic ring in the liquid crystals. A dichroic ratio Dsp was calculated according to the following formula:

$$Dsp = -log(Rs)/-log(Rp)$$

The result of the calculation was shown in Table 3.

COMPARATIVE EXAMPLE 1

A material for an alignment layer of PSI2201 (made by Chisso Petrochem Co.) was applied on two substrates (20×30×0.1 mm) having electrodes of 2 cm$^2$ in area thereon. A thickness of the alignment layer was adjusted to 50 nm. These substrates were arranged to face each other with a spacer interposed between the substrates at a space of 4 μm. The substrates were bonded to each other. The same liquid material as that used in Example 1 was poured with the space vacuumized. Thus a liquid crystal cell was prepared.

A pretilt angle of the liquid crystal cell was measured by use of a magnet of magnet intensity of 1 T by means of a magneto-capacitive null method. However a pretilt angle could not be measured because a capacitance did not changed in spite of rotation of the liquid crystal cell in the magnetic field.

COMPARATIVE EXAMPLE 2

The same two substrates as those in Comparative Example 1 were used. An alignment layer was formed on those substrates in a manner similar to that in Comparative Example 1.

These substrates were arranged to face each other with a spacer interposed between the substrates at a space of 4 μm. The substrates were bonded each other. The same liquid material as that used in Example 1 was poured with the space vacuumized. Thus a liquid crystal cell was prepared.

A pretilt angle of the liquid crystal cell was measured by means of a crystal rotation method. However an asymmetric fringe was given. Therefore a pretilt angle could not be measured because an incident angle which drew symmetric fringe could not be specified.

(Preparation of Calibration Curve for pretilt angle)

The cells for calibration curve were prepared as follows. Alignment layers (50 nm thickness) were formed on transparent electrodes on two glass substrates (20 mm×30 mm×1.1 mm) by use of materials shown in Table 1. PVA117 in Table 1 was made by Kuraray Co. The two substrates were bonded with the two alignment layers facing each other. The space between the substrates was filled with the same liquid crystals as those in Example 1–3. A thickness of the liquid crystal layer was 20 μm.

The cells for the calibration curve were subjected to a measuring process according to a crystal rotation method to give pretilt angles. The results were shown in Table 1 below.

TABLE 1

| (Pretilt angle measured by a crystal rotation method (liquid crystal layer thickness of 20 μm)) | |
|---|---|
| Alignment layer | Pretilt angle |
| PVA117 | 0° |
| SE150 | 4.5° |
| SE4110 | 5.0° |
| PSI2201 | 7.5° |

On the other hand three other liquid crystal cells for the calibration curve were prepared in a manner similar to the above cells for the calibration curve except that one of the substrates is a germanium substrate instead of a glass substrate having transparent electrode. Thus obtained cells were subjected to a measuring process of dichroic ratio Dsp in a manner similar to Examples 1–3. The results were shown in Table 2 below.

TABLE 2

| Alignment layer | Dichroic ratio (Dsp) |
|---|---|
| PVA117 | 0.30 |
| SE150 | 0.50 |
| SE4110 | 0.53 |
| PSI2201 | 0.72 |

Figure 2:
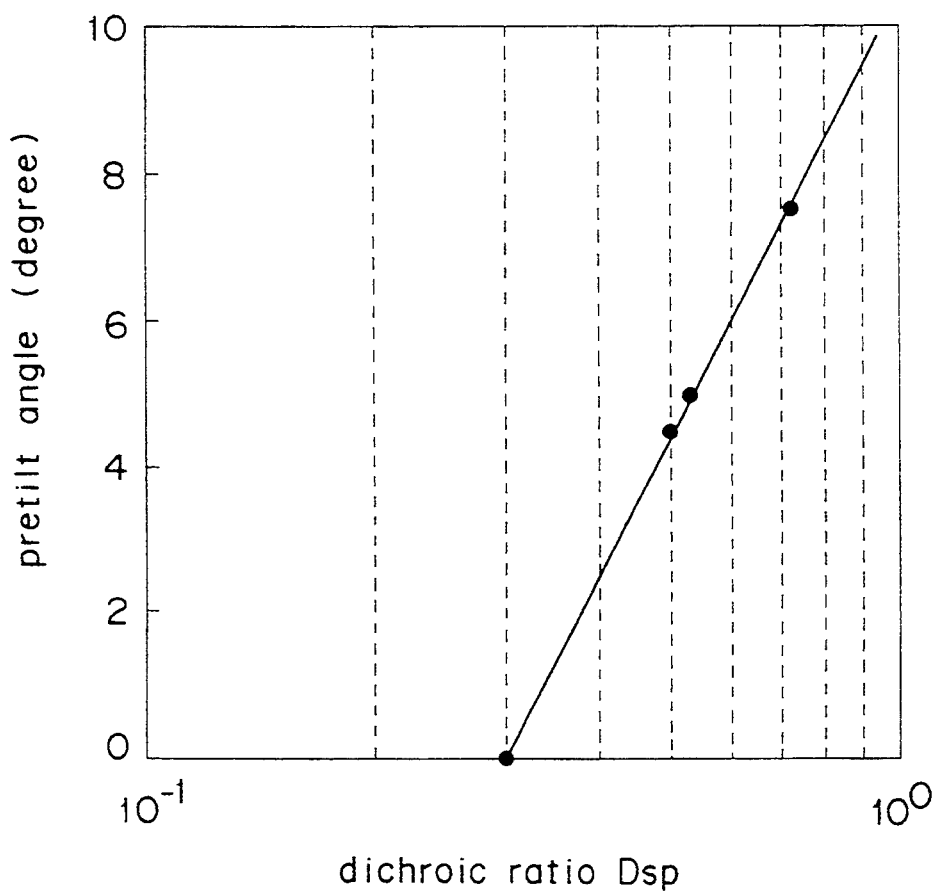
FIG. 2 is a graph showing a calibration curve for a pretilt angle.

A relationship between the pretilt angles and the dichroic ratios Dsp was shown in FIG. 2.

(Measurement of pretilt angle)

Pretilt angles of the liquid crystal cells prepared in Examples 1–6 were measured on the basis of the calibration curve. The results were shown in Table 3.

It can be clearly understood that the results of measurement on pretilt angles correspond well to the results given by conventional method for measuring a pretilt angle.

TABLE 3

|  | Alignment Layer | Dichroic Ratio | Pretilt Angle |
|---|---|---|---|
| Example 1 | SE150 | 0.50 | 4.5° |
| Example 2 | SE4110 | 0.53 | 5.0° |
| Example 3 | PSI2201 | 0.72 | 7.5° |
| Example 4 | SE150 | 0.51 | 4.5° |
| Example 5 | SE4110 | 0.54 | 5.0° |
| Example 6 | PSI2201 | 0.74 | 7.5° |

What is claimed is:

1. A process for measuring a pretilt angle in which an alignment layer and a liquid-crystal layer each of which has a refractive index smaller than that of a substrate are laminated on the substrate, a polarized light is emitted into the substrate and made to be reflected on an interface between the substrate and the alignment layer, a reflectance, which is given by dividing a reflected-light strength with a liquid crystal layer by that without a liquid crystal layer, is measured, and a ratio of logarithm of reflectances of linear polarized lights crossing each other is calculated.

2. A process for measuring a pretilt angle of claim 1, in which the polarized light has a wavelength in the region of infrared rays.

3. A process for measuring a pretilt angle of claim 1, in which the alignment layer is formed of a polyimide resin the surface of which is subjected to a rubbing process.

4. A process for measuring a pretilt angle in which an alignment layer which has a refractive index smaller than that of a substrate is formed on the substrate, a liquid crystal layer is formed on the alignment layer which has a refractive index smaller than that of the substrate while the alignment layer is kept horizontal, a polarized light is emitted into the substrate and made to be reflected on an interface between the substrate and the alignment layer, a reflectance, which is given by dividing a reflected-light strength with a liquid crystal layer by that without a liquid crystal layer, is measured, and a ratio of logarithm of reflectances of linear polarized lights crossing each other is calculated.

5. A process for measuring a pretilt angle of claim 4, in which the polarized light has a wavelength in the region of infrared rays.

6. A process for measuring a pretilt angle of claim 4, in which a sectional view of the substrate is trapezoid.

7. A process for measuring a pretilt angle of claim 4, in which the alignment layer is formed of a polyimide resin the surface of which is subjected to a rubbing process.

8. An apparatus for measuring a pretilt angle which comprises:
 a photo system composed of a light source which emits a linear polarized light into a substrate,
 a detecting system for measuring reflectance of light reflected inside the substrate, and
 a data-processing system which calculates a pretilt angle from a ratio of logarithm of reflectances of linear polarized lights crossing each other.

9. An apparatus for measuring a pretilt angle of claim 8, in which the polarized light has a wavelength in the region of infrared rays.

10. An apparatus for measuring a pretilt angle which comprises:
 a substrate-keeping system keeping a liquid-crystal layer on a substrate horizontal,
 a photo system composed of a light source which emits a linear polarized light into the substrate,
 a detecting system for measuring reflectance of light reflected inside the substrate, and
 a data-processing system which calculates a pretilt angle from a ratio of logarithm of reflectances of linear polarized lights crossing each other.

11. An apparatus for measuring a pretilt angle of claim 10, in which the polarized light has a wavelength in the region of infrared rays.

* * * * *